United States Patent [19]

Cummings

[11] Patent Number: 4,526,903

[45] Date of Patent: * Jul. 2, 1985

[54] PROCESS FOR THE PRODUCTION OF SYNTHESIS GAS FROM COAL

[75] Inventor: Donald R. Cummings, Sydney, Australia

[73] Assignee: Dut Pty Limited, Burradoo, Australia

[*] Notice: The portion of the term of this patent subsequent to Jul. 26, 2000 has been disclaimed.

[21] Appl. No.: 339,007

[22] Filed: Jan. 12, 1982

[30] Foreign Application Priority Data

Jan. 23, 1981 [GB] United Kingdom ............... 8102010

[51] Int. Cl.$^3$ .................. C10K 3/04; C07C 29/15
[52] U.S. Cl. ..................... 518/704; 48/210; 48/214 R; 252/373
[58] Field of Search ............. 518/703, 704, 705, 702; 252/373; 48/202, 214 R, 210

[56] References Cited

U.S. PATENT DOCUMENTS

| | | | |
|---|---|---|---|
| 3,551,123 | 12/1970 | Stotler | 48/214 R |
| 4,087,449 | 5/1978 | Marschner | 518/703 |
| 4,199,327 | 4/1980 | Hempill | 48/202 |
| 4,211,540 | 7/1980 | Netzer | 48/202 |
| 4,211,669 | 7/1980 | Eakman et al. | 252/373 |
| 4,395,495 | 7/1983 | Cummings | 518/728 |

Primary Examiner—Peter Kratz
Attorney, Agent, or Firm—Browdy and Neimark

[57] ABSTRACT

The overall conversion of coal to synthesis gas by pressurized counter-current gasification is improved by steam reforming the methane values in the gas and heating the steam reformer by means of a fluidized bed combustor fuelled by the coal fines which are too small to be employed in the gasification step. Coal can be crushed to increase the proportion of fines and/or conditions for gasifications and/or steam reforming varied so as to consume lump coal and fines in the desired ratio. The product gas may be used for methanol synthesis.

15 Claims, 3 Drawing Figures

PROCESS FOR THE PRODUCTION OF SYNTHESIS GAS FROM COAL

The present invention relates to a process for the production of synthesis gas from coal, for example for the subsequent production of methanol. In particular the process is concerned with counter-current gasification of coal and involves a subsequent steam reforming step for which heat is supplied by means of a fluidised bed.

The term coal as used herein means not only anthracitic, bituminous and brown coal but also lignite.

Counter-current coal gasifiers such as the gasifier developed by Lurgi Kohle and Mineraloltechnik GmbH have been in existence for some decades and have been used to convert coal to hydrogen and oxides of carbon which may be purified and which in turn are used as synthesis gas for reactions such as synthesis via the Fischer Tropsch process to produce liquid hydrocarbons, synthesis to produce methanol, or via the OXO synthesis route to produce higher alcohols. The gases may also be converted to a hydrogen containing gas suitable for hydrogenation reactions, or alternatively used as such or suitably purified and possibly converted to hydrogen for the reduction of metallic ores.

The process using such gasifiers, and in particular the process used by Lurgi Kohle and Mineraloltechnik GmbH, is well established and it is now available in a form which has been developed by the British Gas Council in which the ash residue is removed from the gasifier as a slag.

A desirable feature of the process is that it is capable of being operated under elevated pressure. This is of considerable benefit where subsequent processing steps and allied processes using the produced gases are also operated under pressure since the production of the raw synthesis gas under pressure can result in higher efficiencies due to reduction of compression requirements and lower capital cost due to the use of compact equipment.

A further desirable feature of the counter-current process is that the gases leave the gasifier at a relatively low temperature and thus the heat in the high temperature reactants in the base of the gasifier is transferred back to the descending fuel bed and reactions such as methanation occur above the high temperature zone. The methanation reaction and the rising hot gases preheat and partially carbonise the coal entering the top of the gasifier thus producing together with the gases resulting from the reaction at the base of the column additional gases and liquid from further gas reactions and the drying and carbonisation of the feed coal. This counter-current flow results in a high thermal efficiency for the gasifier.

There are, however, two major deficiencies in the pressurised fixed bed counter-current gasifier, namely, the production of increasing quantities of methane as the gasifier pressure is increased and the inability of such gasifiers readily to accept the coal fines which are produced as a normal consequence of mining operations. In addition, there is the problem that the process produces an aqueous effluent which contains impurities such as phenol, suspended tar and dissolved ammonia and the further problem that in some instances the co-produced tars and in particular the heavier fractions may be difficult to dispose of.

The prensence of methane in synthesis gas is not desirable where the gas is to be used in reactions, such as the production of methanol, ammonia or hydrocarbons via the Fischer Tropsch process or for ore reduction, where conversion is incomplete and unreacted gas is therefore recycled to the reactor to form a so-called synthesis loop. This is because the methane is non-reactive and if not eliminated from the synthesis gas prior to the reaction, synthesis or ore reduction, accumulates in the circulating gases and must be purged from the synthesis loop together with some of synthesis gas.

Current operating pressures for the Lurgi non-slagging and British Gas/Lurgi slagging gasifiers are about 20 to 30 bar but it would be desirable to operate these gasifiers at higher pressures, up to about 100 bar and possibly above. As the pressure is increased there is an improvement in coal gasified per unit of fed oxygen as well as an increase in the output and efficiency of a given size reactor. In addition, as gasification pressure is increased, the need for downstream gas compression is reduced. However, as the pressure is increased there is also an increase in the amount of methane formed which, as stated above, is undesirable for the production of synthesis gas and synthesis gas derived products. As a result of this, despite the advantages in operating at the higher pressure range, where the gasifiers are used for producing synthesis gas, the pressure of operation is kept to the 20–30 bar pressure range and pressures of up to 100 bar are planned only for applications such as the production of synthetic natural gas where the presence of methane is desirable.

It is known, e.g. in the production of methanol from synthesis gas, that any methane values in the gas purged from the methanol synthesis loop may be converted to produce more synthesis gas by steam reforming but a significant part of the purge gas, about 40%, is required to fuel the steam reformer, thereby limiting the potential yield of additional synthesis gas by this route.

Fixed bed counter-current gasifiers require coal above a certain size for satisfactory operation and for this reason it is necessary to separate from the coal supply fines smaller than about 5 mm in size. Such fines generally constitute about 20–40% of the coal output from a mine and further fines are produced during handling and screening the coal and in crushing oversize pieces. Accordingly, maximisation of the production of synthesis gas from run-of-mine coal in a plant employing a pressurised counter-current gasifier generally requires not only a steam reformer to convert the methane values in the gas produced by this gasifier but also the provision of an alternative form of gasifier, such as the kind developed by Texaco, which is capable of utilizing the fines.

The present invention provides a process which avoids the above-mentioned problems associated with the use of counter-current gasifiers and improves the overall utilisation of coal in the production of synthesis gas by a counter-current coal gasification process without the capital expense of having to employ an additional gasifier. In the process of the invention, the fines are used as fuel for a fluidised bed combustor employed to provide the heat for steam reforming the methane values in the gas produced by the counter-current gasification.

Thus, according to the present invention there is provided a process comprising the steps of dividing lump coal suitable for counter-current gasification from a coal supply comprising such lump coal and fines, performing counter-current gasification of lump coal divided from the coal supply at superatmospheric pressure to form a gas comprising hydrogen oxides of carbon and also containing methane values and subsequently steam reforming at least a portion of said methane values in a reactor at least partially immersed in a fluidised bed of finely divided solid, and wherein at least some of the heat for the steam reforming step is provided by heating the fluidised bed by combustion of fines divided from the lump coal as a result of the first step. The use of high pressure, above 30 bar, is advantageous because, as stated above, the need for compression prior to subsequent processing is avoided. The extra methane produced does not lower the efficiency of the process because it is converted in the steam reforming step to oxides of carbon and hydrogen which can be recycled for further processing. By appropriate choice of conditions, all or substantially all of the coal may be used in the process as the lump coal is fed to the gasifier while the fines are used to fuel the fluidised bed.

The ratio of lump coal to fines in the coal supply may be controlled so as to be substantially equal to the ratio of consumption of lump coal in the gasification step to the rate of combustion of fines in providing heat for the steam reforming step. For example, coal may be crushed to increase the proportion of fines.

By-products from the gasification step such as hydrogen sulphide, dissolved tar and phenols which are normally waste products requiring disposal, may also be used as supplementary fuel for heating the fluidised bed.

The fluid bed combustor for the steam reforming may employ an atmospheric pressure fluid bed combustor of simple 'plug flow' design or it may employ the separate fluidising and combustion gas zones of the 'fast bed' combustor as developed by Batelle Institute and Lurgi. A preferred arrangement for the combustor is the pressurised fluid bed combustor as generally described in U.K. patent publication No. 2055891.

The gasification step of the process need not be carried out using the Lurgi or British Gas type of gasifiers and alternatively other kinds of counter-current gasifiers could be used. For example the gasification could be performed using two or more single stage fluid beds arranged in counter-current flow. Such alternatives have in the past had the problem that, particularly at high pressures, an undesirable amount of methane is produced.

By means of this invention coal fines and fine low grade coal (which term includes lignite) may be used to provide the bulk of the fuel for providing the heat for the reformer. The process thereby eliminates or substantially eliminates the need to use part of the methane containing gas to fuel the reformer and thereby increases the amount of synthesis gas produced for a given counter-current gasifier and a given quantity of lump coal fed to the gasifier, when compared to the conventional processes.

By using the process of the invention the pressure of the counter-current gasifier may be increased to pressures above 30 bar and to or above 100 bar at which pressures such gasifiers would not normally be suited to the manufacture of synthesis gas. By operation of the gasifier at higher pressures the output of the gasifier can be increased, the utilisation of oxygen per unit of lump coal gasified increased and the thermal efficiency of the conversion of lump coal to crude synthesis gas increased. The increased amount of methane produced by operating at such higher pressures is no longer a problem since it is reformed using coal fines. The overall ratio of fines to lump coal consumption and the production of synthesis gas from a given amount of lump coal are thus both increased. As a result of this feature, the operating conditions, especially pressure of gasification and steam reforming may be selected to ensure that the rates of feed of lump and fine coal to the gasifier and reformer respectively, are consistent with the available ratio of lump and fines from the related mining operation and any subsequent crushing of the lump coal.

The process of the invention may incorporate a methanol synthesis step where gas containing hydrogen and oxides of carbon and produced by the gasification step, is supplied to a methanol synthesis zone. Advantageously, the methanol synthesis step is performed on gas from the gasification step in a synthesis zone with recycle of unreacted gases and the steam reforming step is performed on a purge stream containing methane values and taken from the methanol synthesis recycle stream and reformed gas is returned to the methanol synthesis zone. Alternatively, however, gas from the gasification step may first be subjected to steam reforming to convert methane values therein to additional hydrogen and/or oxides of carbon and the reformed gas is thereafter subjected to said methanol synthesis step.

An important feature of the invention is that it can be employed to improve the hydrogen to oxides of carbon ratio towards the optimum required for methanol synthesis. The hydrogen to oxides of carbon ratio in the synthesis gas produced from gasifiers is usually below that required for methanol synthesis and has to be adjusted e.g. by shift reaction of carbon monoxide and/or the removal of carbon dioxide by scrubbing. The hydrogen to oxides of carbon ratio in the gas produced by the steam reforming of methane, on the other hand, is generally above that required for methanol synthesis. Accordingly, by means of the invention, it is possible to produce a gas in which the ratio approaches the ideal for methanol synthesis by utilising the combination of gas from the gasification and gas from the reformer as the methanol synthesis feed and adjusting the pressure of the gasification which in turn controls the concentration of methane available for steam reforming in the gas so produced.

Hydrogen sulphide present in the synthesis gas leaving the gasifier may be removed therefrom and effectively incinerated to sulphur oxides by injection into the fluidised bed combustor zone, thus eliminating the need for a separate incinerator system or sulphur recovery plant. The fluidised bed may include an absorbent for the sulphur oxides.

Inert gases such as nitrogen and argon which enter the process as impurities, e.g. in the oxygen used for the gasification process and/or as nitrogen contained in the coal, and which build up in a synthesis loop such as in the production of methanol, may be effectively separated by taking part of the reformed gas leaving the reformer and separating the gases by known means such as a shift reaction followed by carbon dioxide removal by scrubbing followed by low temperature separation of the remaining hydrogen, nitrogen, argon and methane with the possible return to the process of part or all of the hydrogen, methane and carbon dioxide streams.

By means of this invention all or a significant portion of any aqueous phenolic effluent and in particular tar/water emulsions, produced as by-products of the counter-current gasification may be fed to the combustion zone of the fluid bed combustor. In particular, such effluent may be used as a slurrying agent for the fines and/or other solid fuel employed to heat the fluidised bed.

Any distillation forming part of the treatment of the product from the coal gasification produces a residue containing tar with coal-derived solid impurities. Although the residue has a fuel value it cannot readily be combusted by conventional means, causing a disposal problem. By means of the invention, tar-containing liquid can suitably be withdrawn as a by-product from the coal gasification step and used as fuel to heat the fluidised bed.

The invention will now be described, by way of example, with reference to the accompanying drawings in which.

Figure 1:
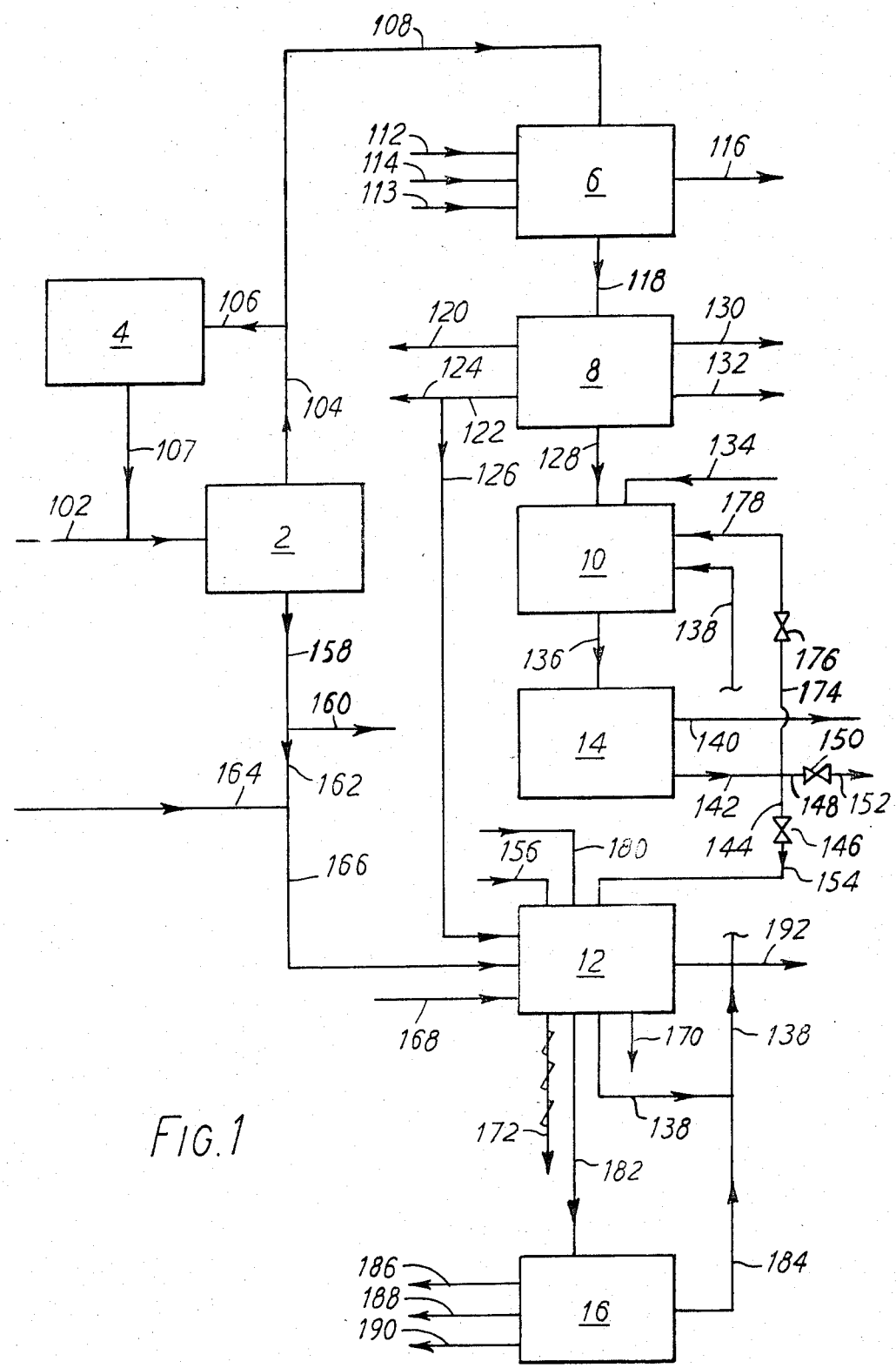
FIG. 1 is a block flow diagram of one embodiment of the process of the invention.

Referring to FIG. 1, the diagram illustrates a process in which coal is used to produce synthesis gas for methanol manufacture. A coal screening device 2, which receives some coal from an oversize coal crusher 4 supplies coal to a counter-current pressurised gasifier 6. Gas containing hydrogen, oxides of carbon and also some methane values is subsequently passed to a gas purification system 8 and thence to a compressor or group of compressors 10. The compressed gas then travels to a methanol synthesis zone 14 from which unreacted gases are passed through a steam reformer 12 which is heated by means of a fluidised bed as described below. After steam reforming, gases are supplied to separator 16.

Coal is fed via a conveying device 102 to the coal screening device 2 which separates coal into lump coal above 5 mm (or such minimum size as to be suitable for the counter-current gasifier 6) which is removed by conveying device 104, and into fines smaller than the minimum size. Part of the lump coal in 104 may be diverted by conveying device 106 to crusher 4 and the crushed material passed back via conveying device 107 to the conveying device 102. By regulating the amount of lump coal passed to the crusher 4 a controlled ratio of fines to lump coal can be maintained.

The undiverted lump coal in conveying device 104 is passed via conveying device 108 to the pressurised counter-current gasifier 6.

The counter-current gasifier 6 incorporates such devices as feed load hoppers, ash lock hoppers, distribution devices and annulus boilers etc. and could for example be a Lurgi type gasifier with solid ash discharge or a British Gas/Lurgi type slagging gasifier, both types of unit being extensively described in readily available technical literature. Gasification is carried out at superatmospheric pressure with the operating pressure being generally above 5 bar and with the preferred range being between 20 and 100 bar. Oxygen is fed to the gasifier via pipeline 112, steam is fed via pipeline 114 and water is fed via pipeline 113. Ash is removed via conveying device 116 and raw gas produced by the gasification, comprising hydrogen and oxides of carbon with some methane values is removed via pipeline 118.

The raw gas passes to the gas purification system 8 which may be designed in accordance with established practice. The gas is cooled to remove tars which leave by pipeline 120 and aqueous liquid which leaves by pipeline 122. Some carbon dioxide and hydrogen sulphide are removed with purified gas in pipeline 128 but the greater part of the hydrogen sulphide and some of the carbon dioxide leave via pipeline 130 after which the hydrogen sulphide could be disposed of by conversion to elemental sulphur or incinerated by known means. In the process illustrated, at least some of the hydrogen sulphide containing gas is passed from pipeline 130 to pipeline 180 and injected into the combustion zone of the fluid bed combustor employed in 12 to heat the steam reformer, where the hydrogen sulphide is combusted to assist in heating the fluidised bed and converted to oxides of sulphur which leave with flue gases in pipeline 170. If desired, the fluid bed may contain dolomite or other sorbent to absorb at least some of the sulphur oxides. Spent sorbent leaves with ash in conveying device 192. The remaining carbon dioxide leaves by pipeline 132 after which it may be vented or produced as a by-product. Purified gas leaves the gas purification system 8 via pipeline 128. The ratio of hydrogen to oxides of carbon produced during the gasification step is controlled by selection of the operating conditions, particularly the pressure in the gasifier 6. The ratio is preferably the optimum for methanol production, allowing for gas supplied to the compressor 10 via lines 134 and 138 from the steam reforming step as described below. The compressor or compressors may be multi-staged units, for example one or more individual units in series, and the compressing section may consist of more than one train in parallel. The compressor(s) may be driven by steam and/or electricity which may be produced e.g. by combustion of any surplus coal fines and/or the compressors may be driven at least in part by the hot gas expander associated with the fluid bed combustor of 12 if the combustor is pressurised.

Carbon dioxide which is obtained from the gas leaving pipeline 132 or from an alternative source and which is sufficiently pure and is supplied at a suitable pressure may also be added to the compressor system 10 via pipeline 134 for compression with the purified gas, should the average carbon oxides to hydrogen ratio in pipelines 128 and 138 be insufficient for optimum methanol synthesis. Additional gas for synthesis is also recirculated to the compressor system via pipeline 178 as described below. The gases in pipeline 138 and 178 may be supplied to the inlet of the compressor or to a suitable intermediate compression stage depending upon the respective pressure of operation of the gasifier 6, the steam reformer 12 and the synthesis reactor system 14.

Combined, compressed, gas for synthesis leaves the compressor system 10 via pipeline 136 and passes to the synthesis reactor system 14. The reactor system 14 consists of a catalyst filled reactor or reactors, suitably tubes, and also heat exchangers, water heaters or boilers, coolers, heat exchangers and separators in accordance with the known methods of constructing such systems. Crude methanol is produced in the synthesis reactor system 14 and is extracted via pipeline 140 after which it may be distilled or suitably treated to remove impurities. Unreacted synthesis gas i.e. hydrogen and oxides of carbon together with inerts such as methane, nitrogen and argon are recovered from the system via pipeline 142 and passed via pipeline 174, valve 176 and pipeline 178 back to the compressor system 10 and thence back to the synthesis reactor system 14. The rate of recirculation may be controlled in a suitable manner by valve 176. Due to this recirculation, the concentrations of inert gas components and in particular the methane content in the reactor system will tend to increase. Accordingly, in order to maintain these concentrations constant, a purge gas stream, rich in methane, generally in the range of 20 to 60% by volume, is withdrawn from the recycle stream and this is passed via pipeline 144, valve 146 and pipeline 154 to the steam reformer 12. The pipeline passes through the heated fluid bed and the methane content in the gas therein is substantially reformed to hydrogen and oxides of carbon. The resultant reformed gas is then passed via pipeline 138 to the compressor section 10.

The fluid bed combustoremployed in 12 may be a substantially ambient pressure combustor but in this example the combustor is pressurised and constructed generally in accordance with the design described in aforementioned British patent publication No. 2055891. The combustor includes suitable coal feed systems which may include coal slurrying and pumping apparatus, provision for ash removal, combustion gas clean-up systems including cyclones or alternative separation equipment, combustion gas cooling, combustion air compression and combustion gas expansion devices, reformer feed gas preheating equipment, reformed gas cooling apparatus, and waste heat boilers and water heaters as necessary, generally in accordance with the arrangement decribed in the patent publication referred to above.

Coal fines from the screening section 2 pass via the conveying device 158 and fines as necessary for steam raising for process steam and process power may be removed via conveying system 160. The remaining fines pass via the conveying system 162 and to this may be added via conveying system 164 lower grades of coal such as washery middlings and possibly washery tailings, which would be suitably sized for conveying. The combined fuels are fed by conveying device 166 to the fluid bed combustor of 12 and air for the combustor is drawn in via duct 168. Sorbent, if used, is provided e.g. in the form of limestone or dolomite. The sorbent or a suitable inert material maintains the necessary bed height in the combustor and is fed to the combustor by conveying device 156. Aqueous phenolic effluent from the gas purifier 8 is passed to the combustor of 12 via pipeline 126 and may be injected by pumping into the combustor or mixed with the coal fines feed and pumped as a fuel slurry component for the combustor. Water for steam production is supplied via pipeline 180. Ash and any spent sorbent is removed from the combustor by conveying device 192 and flue gas leaves via pipeline 170.

Power may be produced by the expansion of the flue gas exiting from the pressurised fluid bed through a turbine and may be provided in the form of shaft power which could be coupled direct to compressor drives in the compression section 10 and possibly the air for the oxygen plant, and/or may be converted to electric power as shown in cable 172 for subsequent use by using electric drives for the compressors and possibly other pumps and electrical devices allied to the process as a whole as desired by a person skilled in the art.

The methane content of the purge gas from the methanol synthesis reactor system is thus constantly removed and subjected to steam reformation in a pipeline 154 passing through the fluid bed combustor of 12, heated mainly by the combustion of coal fines. However, with recirculation, inerts such as nitrogen and argon accumulate in the reaction gases and have to be purged from the system via pipeline 148, valve 150 and pipeline 152. The purge gas may be treated to recover all or part of the hydrogen, carbon oxides and methane values for re-use as reactants or may be used as reformer or general purpose fuel. It is also possible for part of the reformed gases derived from the methane containing gas entering the fluid bed combustor of 12 to be withdrawn via pipeline 182 and pass to the gas separation system 16 which could include any of a wide variety of known processing devices but which in this example consists of a shift reactor to convert carbon monoxide to carbon dioxide, a scrubbing system to remove carbon dioxide and a low temperature gas separation plant to separate nitrogen and argon, both of which leave the unit via pipleine 188. Methane leaves the unit via pipeline 190 and hydrogen leaves the unit via pipeline 184. Hydrogen returns to the compressor and synthesis systems 10 and 14 via pipelines 184 and 138 and recovered methane and possibly carbon dioxide may also be returned to the methanol synthesis loop. The gas separation system 16 would contain the necessary compressors to enable the recycle of the recovered gases.

It will be apparent to those skilled in the art that the fluid bed-heated steam reformer may also be used in a similar manner in conjunction with a counter-current coal gasifier to produce synthesis gas for hydrogen production where the hydrogen may be produced as the final product or alternatively where the hydrogen may be used for hydrogenation purposes and where the hydrogenation reactor system would effectively replace the methanol synthesis reactor 14 in FIG. 1. Alternatively, the synthesis gas may be used in the manufacture of ammonia, hydrocarbons or alcohols, or for the reduction of metallic ores.

The arrangement of FIG. 1 could be modified so as to perform the steam reforming step in 12 before the methanol synthesis step in 14. Gas from the gasifier 6 after purification and compression in compression system 10 could be passed directly to the steam reformer. The steam reformation effected therein would increase the proportion of hydrogen and carbon oxides to the detriment of the proportion of methane so that after separation in separator 16 gas with only a trace of methane and consisting mainly of hydrogen and carbon oxides is supplied to the methanol synthesis zone 14. In this modified version it would be necessary to divide a purge stream from pipeline 142 containing unreacted gases which would mainly be nitrogen and argon with traces of methane.

The process of FIG. 1 is controlled so that the ratio of the rate of supply of lump coal to the gasifier 6 is approximately equal to the rate of combustion of fines in fuelling the fluid bed 12. This is achieved by crushing an appropriate amount of lump coal in the crusher 4 to increase the proportion of fines as necessary and by selecting the operating conditions of the gasifier and fluid bed so as to consume the correct amount of lump coal and fines, respectively. Also, as described above, the relative proportions of hydrogen and oxides of carbon in gas supplied via pipeline 136 to the methanol synthesis zone 14 can be adjusted by varying the operating conditions of the gasifier and are increased by steam reforming. The ratios of the gases may thus be controlled so as to be the optimum for efficient methanol production.

For a typical prior art design of methanol plant using a feed obtained from coal fed Lurgi gasifiers operating at 30 bar and incorporating a Lurgi autothermal reformer to reform the methane values in the gas obtained from the gasifiers, 6,300 Gj/hr of coal feed containing no more than 10-15% fines would produce 162 tonnes per hour of methanol with an overall thermal efficiency of 50.8%.

If the autothermal reformer were eliminated the plant would produce 82.2 tonnes per hour of methanol, 1894 Gj/hr of of SNG (synthetic natural gas) and 468 Gj/hr of tar liquids with an overall thermal efficiency of 63.3%.

By using the arrangement of FIG. 1, the same gasifiers operating for example at 30 bar together with a pressurised fluid bed combustor-heated steam reformer with the combustor operating at 20 bar feed air pressure and the reformer operating at 30 bar pressure, could consume 7,815 Gj/hr of coal having 30 to 35% fines to produce 178 tonnes per hour of methanol and 468 Gj/hr of tar liquids with an overall thermal efficiency of 52.7% and an increase in the effective thermal conversion of the lump fraction of the coal of about 5%.

Figure 2:
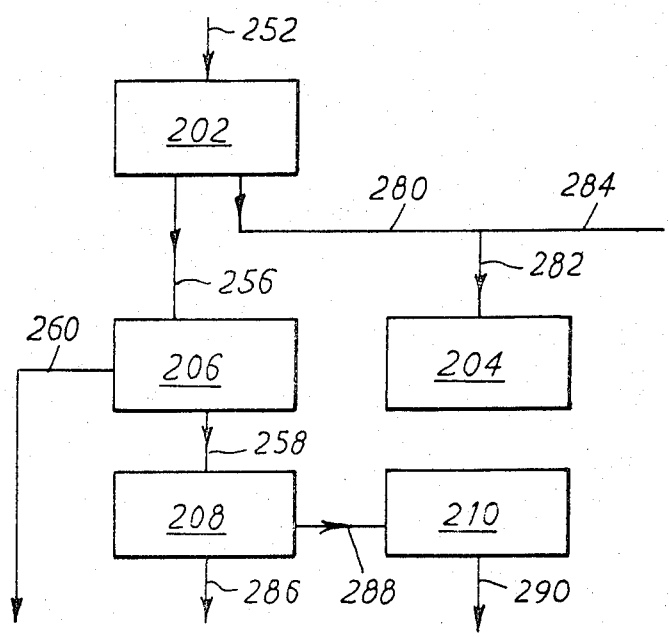
FIG. 2 is a block flow diagram of a prior art process.

FIG. 2 shows a typical arrangement for a conventional prior art counter-current gasifier of the type designed by Lurgi incorporating a coal crushing and screening unit 202, utilities section 204 producing power, steam and oxygen and a gasifier 206 operating at 30 bar and incorporating all the necessary coal feed devices and gas cooling and purification systems. A methanol synthesis unit 208 operates at 70 bar incorporating gas compression and recycling systems, gas cooling, methanol removal and distillation systems and a methanation plant 210 produces synthetic natural gas.

Coal which may have been pre-treated by washing is fed via conveyor system 252 to the crushing and screening unit 202. Coal with a size range between 5 and 50 mm in passed via conveyor system 256 to the gasifier 206 and coal fines smaller than 5 mm are removed by conveyor system 280 and thence either via conveyor 282 to the utilities section 204 as fuel or via conveyor 284 as a surplus coal fines product.

Oxygen and steam are added to the gasifier 206, recovered tar is removed via pipeline 260 and synthesis gas is transferred via pipeline 258 to the methanol synthesis plant 208. Not shown are aqueous effluent and acid gas removal systems.

The methanol synthesis unit 208 produces methanol in pipeline 286 and purge gas in pipeline 288 which is passed to the methanation system 210. Produced synthetic natural gas leaves the methanation system 210 in pipeline 290. The purge gas in pipeline 288 contains untreated methane produced initially in the gasifier 206 together with hydrogen and oxides of carbon and some nitrogen and argon.

For a typical bituminous coal the principal energy flows on an hourly basis for the process of FIG. 2 are as follows:

| Conveyor/Pipeline | Energy flow/hour (G.j.) |
|---|---|
| Conveyor 252 | 8280 G.j. |
| Conveyor 256 | 5400 G.j. |
| Conveyor 282 | 1000 G.j. |
| Conveyor 284 | 1880 G.j. |
| Pipeline 260 | 468 G.j. |
| Pipeline 286 | 1625 G.j. |
| Pipeline 290 | 1894 G.j. |

Figure 3:
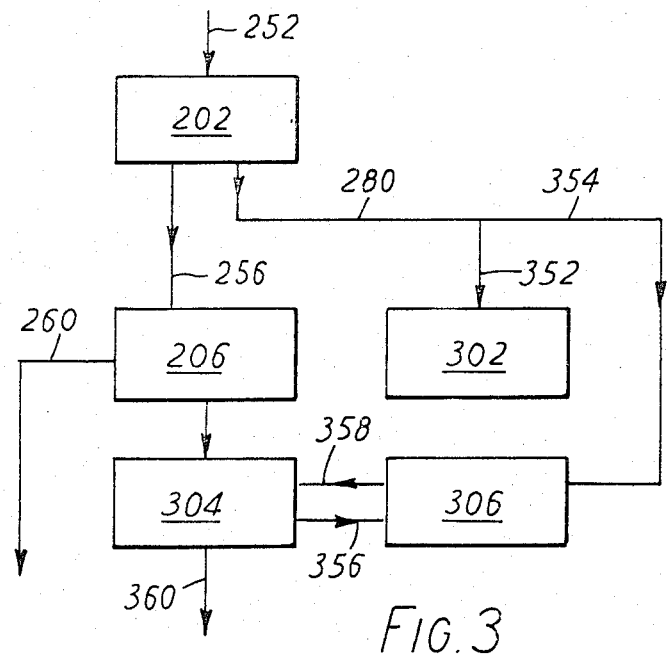
FIG. 3 is a block flow diagram of a second embodiment of the invention obtained by modifying the process of FIG. 2.

FIG. 3 shows the plant in FIG. 1 modified with a revised utilities section 302, an enlarged methanol synthesis unit 304 and unit 306 which is a steam reformer operating at 30 bar pressure and heated by a fluidised bed combustor which is designed to operate with a combustion pressure of 20 bar. The reformer/combustor is similar in design to the unit described in British patent publication 2055891 and incorporates apparatus for fuel slurry preparation, ash removal, air compression, flue gas expansion and heat recovery and process gas heat exchange and cooling systems. Provision is also made for inclusion of circulating gas treatment to remove nitrogen and argon inert gases.

Conveyor 282 in the prior art process is replaced by conveyor 352 and conveyor 284 is replaced by conveyor 354 conveying coal fines to the fluid bed combustor 306. Purge gas line 288 is replaced by pipeline 356 passing purged gas for steam reforming in unit 306 and reformed gas from 306 is returned to the synthesis unit 304 via pipeline 358. The other pipelines and units having the same numbers as FIG. 2 have the same function and flows as those of FIG. 2. The revised energy flows in the modified plant are as follows:

| Conveyor/Pipeline | Energy flow/hour (G.j.) |
|---|---|
| Conveyor 352 | 800 G.j. |
| Conveyor 354 | 2080 G.j. |
| Pipeline 360 | 3633 G.j. |

In addition, up to 80,000 liters per hour of effluent water may be added to the 2080 G.j. per hour of coal being fed to the reformer 306. It will be seen that operation of the process of the invention exemplified in FIG. 3 results in greatly increased energy flow per hour from the methanol synthesis unit 304 in pipeline 360 as compared with the prior art flow rate in line 286 from synthesis unit 208 in FIG. 2.

I claim:

1. A process for the production of synthesis gas from coal comprising the steps of
   (a) dividing lump coal suitable for counter-current gasification from a coal supply comprising such coal and fines;
   (b) performing counter-current gasification of lump coal divided from the coal supply at superatmospheric pressure to form a gas comprising hydrogen and oxides of carbon and also containing methane values; and
   (c) subsequently steam reforming at least a portion of said methane values in a reactor at least partially immersed in a fluidized bed of finely divided solid; wherein at least some of the heat for the steam reforming step is provided by heating the fluidized bed by combustion of fines divided from the lump coal as a result of the first step.

2. A process as claimed in claim 1, wherein the gasification step is operated at a pressure above 30 bar.

3. A process as claimed in claim 1, wherein the ratio of lump coal for the gasification step to fines divided therefrom in the first step is controlled so as to be substantially equal to the ratio of the rate of consumption of lump coal in the gasification step to the rate of combustion of fines in providing heat for the steam reforming step.

4. A process as claimed in claim 3, wherein coal is crushed to decrease the proportion of lump coal for the gasification step.

5. A process as claimed in claim 4, wherein at least a part of the lump coal divided from the coal supply in the first step is crushed and the crushed material is returned to the said first step.

6. A process as claimed in claim 1, wherein the operating conditions of the steam reforming step and/or the gasification step are adjusted to conform to the ratio of lump coal for the gasification step to fines divided therefrom whereby substantially all the fines are consumed in providing heat for the steam reforming step by heating the fluidised bed.

7. A process as claimed in claim 1, wherein said gas formed in the coal gasification step contains hydrogen sulphide and hydrogen sulphide values from said gas are removed in a by-product stream and used as supplementary fuel to heat the fluidised bed.

8. A process as claimed in claim 7, wherein the fluidised bed contains an absorbent for sulphur containing components in the gases resulting from the combustion of said hydrogen sulphide containing gas.

9. A process as claimed in claim 1, wherein supplementary fuel to heat the fluidised bed is provided from tar-containing liquid withdrawn as a by-product stream from the coal gasification.

10. A process as claimed in claim 1, wherein supplementary fuel to heat the fluidised bed is provided from an aqueous phenolic stream withdrawn as a by-product from the coal gasification.

11. A process as claimed in claim 1, wherein at least a portion of the fines and/or other solid fuel for heating the fluidised bed is supplied as a slurry in an aqueous stream including an aqueous by-product from the coal gasification step.

12. A process as claimed in claim 1, wherein gas containing hydrogen and oxides or carbon and produced by the gasification step is subjected to a methanol synthesis step.

13. A process as claimed in claim 12, including performing said methanol synthesis step on gas from the gasification step in a synthesis zone with recycle of unreacted gases, performing the steam reforming step on a purge stream containing methane values and taken from the methanol synthesis recycle stream, and returning reformed gas to the methanol synthesis zone.

14. A process as claimed in claim 12, wherein the hydrogen content and/or oxides of carbon content of gas recovered from the coal gasification step and containing methane values is increased by subjecting said gas to said steam reforming step and the reformed gas is thereafter subjected to said methanol synthesis step.

15. A process as claimed in claim 13 or 14, wherein the feed to the methanol synthesis step comprises a mixture of a first stream containing hydrogen and oxides of carbon obtained by the gasification and a second stream containing hydrogen and oxides of carbon and obtained from the steam reformer and the pressure of the gasification step is adjusted to control the amount of methane produced thereby and to give a desired ratio of total hydrogen to total oxides of carbon in the gas mixture.

* * * * *